United States Patent
Al-Muaili et al.

(10) Patent No.: US 11,788,951 B2
(45) Date of Patent: Oct. 17, 2023

(54) TESTING METHOD TO EVALUATE COLD FORMING EFFECTS ON CARBON STEEL SUSCEPTIBILITY TO HYDROGEN INDUCED CRACKING (HIC)

(71) Applicant: Saudi Arabian Oil Company, Dhahran (SA)

(72) Inventors: Saad Al-Muaili, Dhahran (SA); Khalid Ali Babakri, Dhahran (SA); Mohammed Al-Anezi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 417 days.

(21) Appl. No.: 17/207,283

(22) Filed: Mar. 19, 2021

(65) Prior Publication Data

US 2022/0299424 A1 Sep. 22, 2022

(51) Int. Cl.
G01N 17/00 (2006.01)
G01N 3/20 (2006.01)
G01N 33/2045 (2019.01)

(52) U.S. Cl.
CPC ............ *G01N 17/006* (2013.01); *G01N 3/20* (2013.01); *G01N 2203/0023* (2013.01); *G01N 2203/0066* (2013.01)

(58) Field of Classification Search
CPC .......... G01N 3/08; G01N 17/006; G01N 3/20; G01N 2203/0023; G01N 2203/0066;
(Continued)

(56) References Cited

U.S. PATENT DOCUMENTS 4,153,454 A 5/1979 Emi et al.
4,245,698 A 1/1981 Berkowitz et al.
(Continued)

FOREIGN PATENT DOCUMENTS

CA 3043585 A1 5/2018
CN 103484642 B 1/2015
(Continued)

OTHER PUBLICATIONS

NACE TM0177-2016 Laboratory Testing of Metals for Resistance to Sulfide Stress Cracking and Stress Corrosion Cracking in H2S Environments, 2016, 77 pages.
(Continued)

*Primary Examiner* — Brandi N Hopkins
(74) *Attorney, Agent, or Firm* — Bracewell LLP; Constance G. Rhebergen; Keith R. Derrington

(57) ABSTRACT

A plate specimen is extracted from a qualified HIC resistant material having a Heat number. The plate specimen is supported on a female die of a guided bend system and a force is applied with a male die of the guided bend system to a predetermined middle portion of the plate specimen to develop a U-shaped bent portion in the plate specimen. A curved sample is extracted from the predetermined middle portion having the U-shaped bent portion, the curved sample simulates a cold forming ratio of a line pipe having a particular pipe diameter that is to be subsequently manufactured from the qualified Heat number. A standardized HIC test on the extracted curved sample. Respective values of Crack Length Ratio (CLR), Crack Sensitivity Ratio (CSR) and Crack Thickness Ratio (CTR) are calculated for the curved sample subsequent to the standardized HIC test on the curved sample. The qualified Heat number is validated for manufacturing the line pipe having the particular pipe diameter in response to determining that the calculated (Continued)

respective values of CLR, CSR, and CTR not greater than the corresponding predetermined maximum threshold values for the CLR, CSR, and CTR.

20 Claims, 4 Drawing Sheets

(58) Field of Classification Search
CPC .......... G01N 1/04; C21D 9/46; C21D 8/0226; C21D 9/08; C21D 8/10; C21D 8/105; B23K 11/0006; Y02P 10/25; Y02P 10/20; C22C 19/055; C22C 38/04; C22C 38/00; C22C 38/02; C22C 38/44
See application file for complete search history.

(56) References Cited

U.S. PATENT DOCUMENTS

| | | | |
|---|---|---|---|
| 4,942,922 | A | 7/1990 | Redmerski et al. |
| 5,555,916 | A | 9/1996 | Kushida |
| 5,556,594 | A | 9/1996 | Frank et al. |
| 5,728,943 | A | 3/1998 | Colter et al. |
| 5,993,570 | A | 11/1999 | Gray |
| 6,149,862 | A | 11/2000 | Gliklad et al. |
| 7,723,643 | B2 | 5/2010 | Hackel et al. |
| 8,002,910 | B2 | 8/2011 | Tivelli et al. |
| 8,262,767 | B2 | 9/2012 | Numata et al. |
| 8,356,857 | B2 | 1/2013 | Ralston et al. |
| 8,821,653 | B2 | 9/2014 | Anelli et al. |
| 8,956,857 | B2 | 2/2015 | Heyduk et al. |
| 9,222,871 | B2 | 12/2015 | Roumeau et al. |
| 9,540,717 | B2 | 1/2017 | Nakata et al. |
| 9,568,407 | B2 | 2/2017 | Pittam et al. |
| 9,644,248 | B2 | 5/2017 | Anelli et al. |
| 9,657,365 | B2 | 5/2017 | Anelli et al. |
| 9,931,715 | B2 | 4/2018 | Kanasaki et al. |
| 10,295,508 | B2 | 5/2019 | Traidia et al. |
| 10,421,545 | B2 | 9/2019 | Hess |
| 10,458,960 | B2 * | 10/2019 | Traidia ................ G01N 29/30 |
| 10,788,461 | B2 | 9/2020 | Mizuno et al. |
| 10,866,183 | B2 | 12/2020 | Sherik et al. |
| 11,235,427 | B2 | 2/2022 | Al-Muaili et al. |
| 2005/0061404 | A1 | 3/2005 | Erike |
| 2007/0089813 | A1 | 8/2007 | Tivelli et al. |
| 2009/0025839 | A1 | 1/2009 | Watanabe et al. |
| 2011/0100131 | A1 | 5/2011 | Brown et al. |
| 2011/0214932 | A1 | 9/2011 | Ralston et al. |
| 2014/0238145 | A1 | 8/2014 | Tran et al. |
| 2014/0299235 | A1 | 10/2014 | Anelli et al. |
| 2014/0299236 | A1 | 10/2014 | Anelli et al. |
| 2015/0307049 | A1 | 10/2015 | Kwon |
| 2017/0191969 | A1 * | 7/2017 | Traidia ................ G01N 29/04 |
| 2018/0186456 | A1 | 7/2018 | Hess |
| 2018/0217049 | A1 | 8/2018 | Sherik et al. |
| 2018/0340913 | A1 * | 11/2018 | Mizuno ............. G01N 29/265 |
| 2018/0364138 | A1 | 12/2018 | Traidia et al. |
| 2019/0024206 | A1 * | 1/2019 | Kim .................... C22C 38/58 |
| 2019/0113482 | A1 | 4/2019 | Traidia et al. |
| 2020/0095649 | A1 | 3/2020 | Cha et al. |
| 2020/0377979 | A1 | 3/2020 | De |
| 2021/0054473 | A1 | 2/2021 | Pathak et al. |
| 2021/0229221 | A1 | 7/2021 | Al-Muaili et al. |
| 2022/0010403 | A1 | 1/2022 | Kim |
| 2022/0299424 | A1 | 9/2022 | Al-Muaili et al. |
| 2022/0299425 | A1 | 9/2022 | Al-Anezi et al. |

FOREIGN PATENT DOCUMENTS

| | | |
|---|---|---|
| CN | 106248571 A | 12/2016 |
| CN | 107991455 A | 5/2018 |
| CN | 110333331 A | 10/2019 |
| CN | 115404393 A | 11/2022 |
| EP | 0998591 B1 | 3/2006 |
| EP | 2520680 B1 | 10/2016 |
| JP | 2712119 B2 | 10/1997 |
| JP | 2006275591 A | 10/2006 |
| JP | 2010236930 A | 10/2010 |
| JP | 6048436 B2 | 12/2016 |
| JP | 2017173100 A | 9/2017 |
| RU | 2433189 C2 | 11/2011 |
| WO | 2019180499 A1 | 9/2019 |
| WO | 2020120563 A | 6/2020 |
| WO | 2021154635 A1 | 8/2021 |

OTHER PUBLICATIONS

NACE TM0284-2016 Evaluation of Pipeline and Pressure Vessel Steels for Resistance to Hydrogen-Induced Cracking, 2016, 36 pages.
Saad Al-Muaili, "A370—18 Standard Test Methods and Definitions for Mechanical Testing of Steel Products", Feb. 20, 2019, 50 pages.
Saad Al-Muaili, "E290 Standard Test Methods for Bend Testing of Material for Ductility", Oct. 29, 2020, 10 pages.
Anonymous, "Standard Test Method, Evaluation of Pipeline and Pressure Vessel Steels for Resistance to Hydrogen-Induced Cracking", ANSI/NACE Standard TM0284-2003, Item No. 21215, 2003, 15 pages.
Anonymous, "Standard Test Method, Laboratory Testing of Metals for Resistance to Sulfide Stress Cracking and Stress Corrosion Cracking in H2S Environments", ANSI/NACE Standard TM0177-2005, Item No. 21212, 2005, 43 pages.
Garett Angus, "Hydrogen Induced Damage in Pipeline Steels", Colorado, 2014, 101 pages.
Haase et al., "Fitness-for-Purpose HIC Testing of Heavy Wall Large Diameter Pipes for Midly Sour Applications in the New NACE TM0284-2016 Solution C", Corrosion, New Orleans, Louisiana, Mar. 2017, 5 pages.
International Search Report and Written Opinion of the International Searching Authority issued in the prosecution of International Application No. PCT/US2021/014867, dated Apr. 6, 2021, 16 pages.
Kim et al., "Effects of Microstructural Inhomogeneity on HIC Susceptibility and HIC Evaluation Methods for Linepipe Steels for Sour Service", ASME, Dec. 9, 2014, 6 pages.
Korda et al., "Hydrogen Induced Cracking of APIX52 and X60 Sour Service Steels Subjected to Pre-Strain Under Prolonged H2S Exposure", IOP Conference Series, 2019, 14 pages.

* cited by examiner

TESTING METHOD TO EVALUATE COLD FORMING EFFECTS ON CARBON STEEL SUSCEPTIBILITY TO HYDROGEN INDUCED CRACKING (HIC)

TECHNICAL FIELD

Embodiments relate generally to carbon steel alloys for use in wet sour environments, and particularly relate to a method for testing sour resistance of the carbon steel alloys that have been subjected to cold forming prior to equipment manufacture for wet sour use.

BACKGROUND

Steel alloy materials used in oil and gas equipment for extraction, treatment, transportation and storage of low-quality crude (e.g., oil and gas containing wet hydrogen sulfide ($H_2S$); water and sour gas) are faced with the risk of sudden and severe cracking. That is, when the oil and gas equipment made of steel alloy is exposed to crude containing water and $H_2S$, hydrogen atoms can originate from the anodic dissolution of the material and can diffuse into the steel and induce severe damage. Different forms of cracking may occur, such as HIC, stress oriented hydrogen induced cracking (SOHIC), sulfide stress cracking (SSC), and the like. These cracks can often be difficult to detect in routine inspections and are thus regarded as a higher risk for integrity loss than weight-loss corrosion. Environmental contamination caused by accidents in oil and gas equipment due to such cracking can be very problematic, and may require large restoration costs. To avoid such accidents, it is generally necessary to use steel alloys excellent in resistance to cracking (e.g., HIC resistant steel, sour-resistant steel, and the like, that is resistant to HIC, SOHIC, SSC, and the like) for wet sour environment applications like line pipes, plates, coils, flanges, vessels, and fittings that are used for extraction, treatment, transportation or storage of crude containing water and $H_2S$.

HIC occurs according to the following principle. As a steel surface (e.g., in line pipes, plates, coils, flanges, vessels, and fittings) comes into contact with wet hydrogen sulfide contained in crude oil/gas, corrosion occurs, and hydrogen atoms generated by the corrosion infiltrate and diffuse into the steel to thereby be present in an atomic state in the steel. While the hydrogen atoms in the steel, as described above, are molecularized in the form of hydrogen gas, a gas pressure is generated, causing brittle cracks to occur in a weak structure in the steel (e.g., an inclusion, a segregation, an internal pore, or the like) due to the gas pressure, and when the cracks gradually grow to exceed the endurable strength of the material, breakage occurs. Thus, when reacting with water, $H_2S$ can cause blistering failure and hydrogen embrittlement such as HIC, SOHIC, and SSC. Such failure may decrease the lifetime of the line pipe or other steel alloy wet sour equipment.

Hydrogen induced cracks either follow a linear or stepwise path within the material. However, under certain stress, material composition, and environmental conditions, the cracks can be arranged in a ladder-like array known as SOHIC. As in HIC, SOHIC is caused by atomic hydrogen dissolved in the carbon steel lattice combining irreversibly to form molecular hydrogen. The molecular hydrogen collects at imperfections in the metal lattice, just as in HIC. However, due to either applied or residual stresses (e.g., stress applied during cold work or forming to manufacture (e.g., fabricate, casting and the like) sour service components like line pipes, plates, coils, flanges, vessels, and fittings, the trapped molecular hydrogen produces microfissures which align and interconnect in a through-wall direction. SOHIC can propagate from blisters caused by HIC, SSC, and from prior weld defects. However, neither HIC nor SSC are preconditions for SOHIC. That is, under very corrosive laboratory conditions, even HIC-resistant steels (that have been tested and proved to be resistant to HIC prior to cold forming) have been shown to be susceptible to SOHIC when the HIC-resistant steel has been subjected to applied or residual stress. Thus, carbon steel alloys immune to either SSC or HIC can still suffer from other types of hydrogen embrittlement like SOHIC under certain types of environmental and stress/strain conditions.

Of course, it is desirable to ensure HIC (and SOHIC) resistance of steel alloy materials that are to be used in wet sour applications containing wet hydrogen sulfide. A measure of successful HIC resistance of steel alloy materials to be used in wet sour applications is usually assessed through standardized corrosion tests such as ANSI/NACE TM0284-2016 ("NACE TM0284"), Evaluation of Pipeline and Pressure Vessel Steels for Resistance to Hydrogen-Induced Cracking. NACE TM0284 provides a standard set of test conditions for consistent evaluation of pipeline and pressure vessel steels and compares test results from different laboratories pertaining to the results of the absorption of hydrogen generated by corrosion of steel in wet $H_2S$. NACE TM0284 describes two test solutions, Solution A and Solution B, and includes special procedures for testing small-diameter, thin-wall, electric-resistance welded and seamless line pipe. The test can thus evaluate resistance to hydrogen-induced stepwise cracking, by enabling consistent and standardized evaluation of the steel's susceptibility to HIC in reproducible service conditions.

Conventional testing for HIC under standardized testing conditions like NACE TM0284 may test for SOHIC resistance on finished products (e.g., equipment, components) that have already been manufactured (e.g., cast, cold worked, cold formed, fabricated) from HIC resistant carbon steel alloys. However, it is desirable to test for SOHIC resistance prior to equipment manufacture, while accurately simulating the applied or residual stress the carbon steel alloy is subject to during the equipment manufacture.

SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the disclosed subject matter or to delineate the scope of the disclosed subject matter. Its sole purpose is to present some concepts in a simplified form as a prelude to the more detailed description that is discussed later.

In one embodiment, a method for performing a standardized hydrogen induced cracking (HIC) test on a HIC resistant material for sour service application is provided. The method includes: extracting a HIC sample from a HIC resistant material candidate; performing a standardized HIC test on the HIC sample; calculating respective values of a plurality of predetermined HIC resistance criteria for the HIC sample subsequent to the standardized HIC test on the HIC sample; determining whether the calculated respective values of the plurality of predetermined HIC resistance criteria for the HIC sample are not greater than corresponding predetermined maximum threshold values; qualifying the HIC resistant material candidate for a guided bend process in response to determining that the calculated respective values of the plurality of predetermined HIC resistance criteria for the HIC sample are not greater than the corresponding predetermined maximum threshold values; performing the guided bend process on the qualified HIC resistant material by supporting a plate specimen obtained from the qualified HIC resistant material on a guided bend system and applying force with male and female dies of the guided bend system to develop a predetermined U-shaped bent portion in the plate specimen; extracting a SOHIC sample from the U-shaped bent portion in the plate specimen; performing the standardized HIC test on the SOHIC sample; calculating a value of at least one predetermined SOHIC resistance criteria for the SOHIC sample subsequent to the standardized HIC test on the SOHIC sample; determining whether the calculated value of the at least one predetermined SOHIC resistance criteria for the SOHIC sample is not greater than a corresponding predetermined maximum threshold value; and validating the qualified HIC resistant material for manufacturing a sour service component in response to determining that the calculated value of the at least one predetermined SOHIC resistance criteria for the SOHIC sample is not greater than the corresponding predetermined maximum threshold value.

In another embodiment, the step of extracting the SOHIC sample from the U-shaped bent portion in the plate specimen includes a step of cutting a curved or bent sample having predefined dimensions as per a standardized NACE TM0284 corrosion test from a predetermined middle portion of the plate specimen on which the guided bend process has been performed. In yet another embodiment, a stress applied to the predetermined middle portion of the plate specimen to develop the predetermined U-shaped bent portion simulates a stress applied during a subsequent cold forming to a high stress region of the sour service component.

In yet another embodiment, the manufactured sour service component is a line pipe having a given pipe diameter, wherein the guided bend process is performed on the plate specimen of the qualified HIC resistant material to develop the predetermined U-shaped bent portion whose dimensions simulate dimensions of the line pipe having the given pipe diameter, and wherein the high stress region of the line pipe is substantially at 180° from a weld area of the line pipe. In yet another embodiment, the standardized HIC test is a standardized NACE TM0284 corrosion test, and wherein the SOHIC sample is immersed in a corrosive test Solution A or a corrosive test Solution B, as defined by the NACE TM0284 corrosion test, during the test.

In yet another embodiment, the HIC resistant material candidate is a hot rolled coil or plate of a carbon steel alloy composition that has a particular Heat number and that has not been subjected to cold forming prior to the guided bend process. In yet another embodiment, the SOHIC sample is a curved or bent sample that is extracted from the plate specimen of the qualified HIC resistant material such that a longitudinal direction of the SOHIC sample is aligned with a principal rolling direction of the qualified HIC resistant material. In yet another embodiment, the method further includes: metallographically sectioning the HIC sample into a plurality of pieces subsequent to the standardized HIC test on the HIC sample; analyzing one or more faces of one or more of the plurality of pieces of the HIC sample to calculate a Crack Length Ratio (CLR), a Crack Sensitivity Ratio (CSR), and a Crack Thickness Ratio (CTR), wherein the calculated CLR, CSR, and CTR are the respective values of the plurality of predetermined HIC resistance criteria for the HIC sample calculated subsequent to the standardized HIC test on the HIC sample; metallographically sectioning the SOHIC sample into a plurality of pieces subsequent to the standardized HIC test on the SOHIC sample; and analyzing one or more faces of one or more of the plurality of pieces of the SOHIC sample to calculate a CLR, wherein the calculated CLR is the value of the at least one predetermined SOHIC resistance criteria for the SOHIC sample calculated subsequent to the standardized HIC test on the SOHIC sample.

In yet another embodiment, the predetermined maximum threshold values for the CLR, CSR, and CTR for the HIC sample are preset at 15%, 2%, and 5%, respectively, and wherein the predetermined maximum threshold value for the CLR for the SOHIC sample is preset at 15%, where the HIC resistant material candidate is qualified for the guided bend process in response to determining that the calculated respective values of the CLR, CSR, and CTR for the HIC sample subsequent to the HIC test are not greater than 15%, 2%, and 5%, respectively, and where the qualified HIC resistant material is validated for manufacture of the sour service component in response to determining that the calculated value of the CLR for the SOHIC sample subsequent to the standardized HIC test thereon is not greater than 15%.

In yet another embodiment, the step of qualifying the HIC resistant material candidate for the guided bend process includes a step of qualifying a given Heat number corresponding to the HIC resistant material candidate for the guided bend process, and the step of validating the qualified HIC resistant material includes a step of validating the given Heat number for the manufacture of the sour service component.

In yet another embodiment, the method further includes a step of invalidating the given Heat number for manufacturing the sour service component in response to determining that the calculated value of the at least one predetermined SOHIC resistance criteria for the SOHIC sample is greater than the corresponding predetermined maximum threshold value. In yet another embodiment, the method further includes a step of extracting a plurality of SOHIC samples from the qualified HIC resistant material on which the guided bend process has been performed, wherein the qualified HIC resistant material is validated for manufacturing the sour service component in response to determining that the calculated value of the at least one predetermined SOHIC resistance criteria for each of the plurality of SOHIC samples is not greater than the corresponding predetermined maximum threshold value.

In yet another embodiment, a method for performing a guided bend process on a qualified HIC resistant material is provided. The method includes: extracting a plate specimen from a qualified HIC resistant material having a Heat number; supporting the plate specimen on a female die of a guided bend system and applying a force with a male die of the guided bend system to a predetermined middle portion of the plate specimen to develop a U-shaped bent portion in the plate specimen; extracting a curved sample from the predetermined middle portion having the U-shaped bent portion, wherein the curved sample simulates a cold forming ratio of a line pipe having a particular pipe diameter that is to be subsequently manufactured from the qualified Heat number; performing a standardized HIC test on the extracted curved sample; calculating respective values of a plurality of predetermined SOHIC resistance criteria for the curved sample subsequent to the standardized HIC test on the curved sample; determining whether the calculated respective values of the plurality of predetermined SOHIC resistance criteria for the curved sample are not greater than corresponding predetermined maximum threshold values; and validating the qualified Heat number for manufacturing the line pipe having the particular pipe diameter in response to determining that the calculated respective values not greater than the corresponding predetermined maximum threshold values.

In yet another embodiment, a stress applied by the male die at the predetermined middle portion of the plate specimen during the guided bend process simulates a stress applied during a subsequent cold forming to a region of the line pipe that is substantially at 180° from a weld area of the line pipe. In yet another embodiment, the qualified HIC resistant material is predetermined to be resistant to HIC prior to cold forming based on standardized HIC testing on the HIC resistant material prior to the guided bend process.

In yet another embodiment, the method further includes: metallographically sectioning the curved sample into a plurality of pieces subsequent to the standardized HIC test on the curved sample; and analyzing one or more faces of one or more of the plurality of pieces of the curved sample to calculate a CLR, a CSR, and a CTR, wherein the calculated CLR, CSR, and CTR are the respective values of the plurality of predetermined SOHIC resistance criteria for the curved sample calculated subsequent to the standardized HIC test on the curved sample. In yet another embodiment, the predetermined maximum threshold values for the CLR, CSR, and CTR for the curved sample are preset at 15%, 2%, and 5%, respectively, where the qualified Heat number is validated for manufacturing the line pipe in response to determining that the calculated respective values of the CLR, CSR, and CTR for the curved sample are not greater than 15%, 2%, and 5%, respectively. In yet another embodiment, the predetermined maximum threshold values for the CLR, CSR, and CTR for the curved sample are each preset at 0%, where the qualified Heat number is validated for manufacturing the line pipe in response to determining that the calculated respective values of the CLR, CSR, and CTR for the curved sample are not greater than 0%.

In yet another embodiment, a guided bend system is provided for performing a guided bend process on a qualified HIC resistant material having a Heat number. The system includes: male and female dies having predetermined characteristics, wherein the predetermined characteristics of the male and female dies are preset based on characteristics of a line pipe having a given pipe diameter that is to be subsequently manufactured from the Heat number of the qualified HIC resistant material subjected to the guided bend process by the guided bend system, and wherein the female die is configured to support a plate specimen extracted from the qualified Heat number; and an actuation system that actuates the male die to apply a pressing force to a predetermined middle portion of the plate specimen supported on the female die to develop a U-shaped bent portion in the plate specimen; where the guided bend system applies a stress at the predetermined middle portion of the plate specimen during the guided bend process to simulate a stress applied during a subsequent cold forming to a region of the line pipe that is substantially at 180° from a weld area of the line pipe.

In yet another embodiment, a SOHIC sample is provided for testing resistance to SOHIC, where: the SOHIC sample is extracted as a curved sample from a predetermined middle portion of a plate specimen obtained from a Heat number of a qualified HIC resistant material, wherein the plate specimen has been subject to a guided bend process to develop a U-shaped bent portion at the predetermined middle portion of the plate specimen, and wherein the Heat number has been prequalified to be resistant to HIC based on a standardized NACE TM0284 corrosion test on a HIC sample extracted from the Heat number prior to the guided bend process, where dimensions of the U-shaped bent portion simulate dimensions of a line pipe having a particular pipe diameter that is to be subsequently manufactured from the qualified Heat number, and where a stress applied at the predetermined middle portion during the guided bend process simulates a stress applied during a subsequent cold forming to a region of the line pipe that is substantially at 180° from a weld area of the line pipe.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

Figure 1:
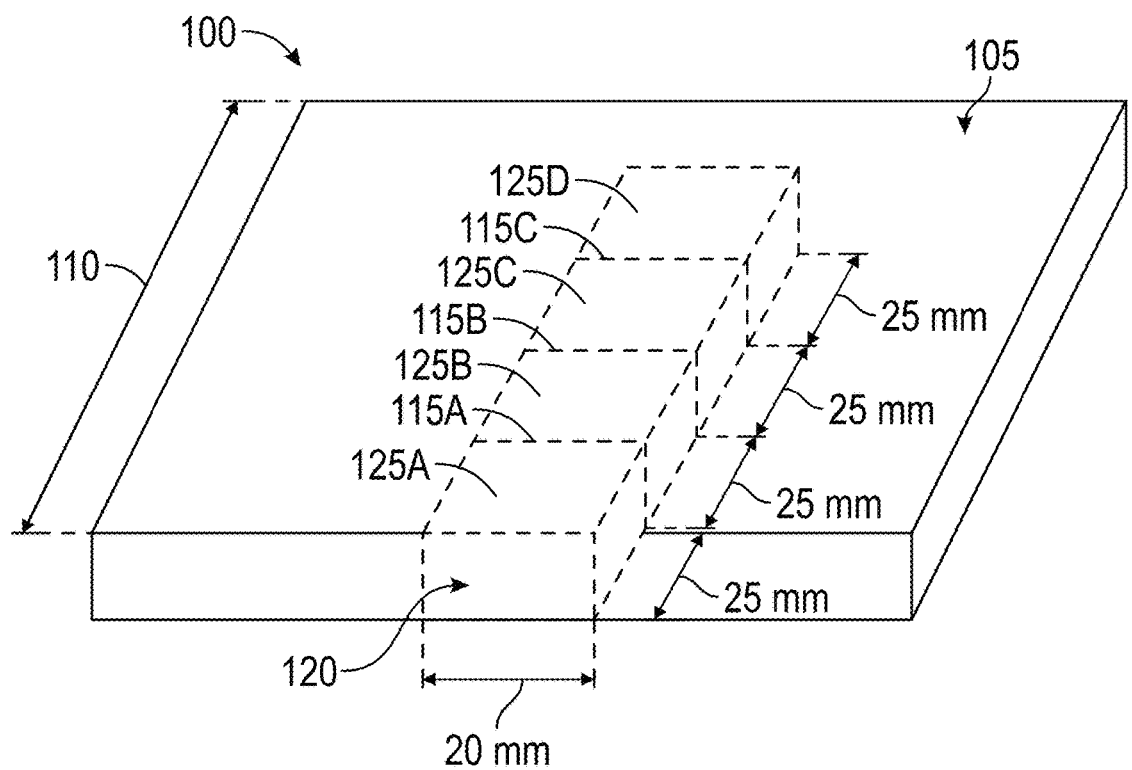
FIG. 1 is a schematic diagram illustrating the orientation and faces to be examined of a sample undergoing standardized HIC testing, in accordance with one or more embodiments.

While certain embodiments will be described in connection with the illustrative embodiments shown herein, the subject matter of the present disclosure is not limited to those embodiments. On the contrary, all alternatives, modifications, and equivalents are included within the spirit and scope of the disclosed subject matter as defined by the claims. In the drawings, which are not to scale, the same reference numerals are used throughout the description and in the drawing figures for components and elements having the same structure.

DETAILED DESCRIPTION

In the following description, for purposes of explanation, numerous specific details are set forth in order to provide a thorough understanding of the inventive concept. In the interest of clarity, not all features of an actual implementation are described. Moreover, the language used in this disclosure has been principally selected for readability and instructional purposes, and may not have been selected to delineate or circumscribe the inventive subject matter, resort to the claims being necessary to determine such inventive subject matter. Reference in this disclosure to "one embodiment" or to "an embodiment" or "another embodiment" means that a particular feature, structure, or characteristic described in connection with the embodiment is included in at least one embodiment of the disclosed subject matter, and multiple references to "one embodiment" or "an embodiment" or "another embodiment" should not be understood as necessarily all referring to the same embodiment.

This disclosure pertains to a testing method and system for evaluating hydrogen embrittlement (e.g., HIC, SOHIC, and the like) on carbon steel alloys subjected to cold forming. Standardized HIC testing is used to qualify different types of carbon steel pipes or other equipment to be used in wet sour petroleum applications containing wet hydrogen sulfide. The HIC test is performed under applicable international standards (e.g., NACE TM0284) to qualify the safe use of carbon steel materials in wet sour environments. Conventionally, when testing for damage (e.g., SOHIC) from applied or residual stresses (e.g., stress applied to hot rolled coil or plate material during pipe or other equipment forming, welding, casting, fabrication and the like) that produce micro-fissures in the carbon steel alloy, the standardized HIC test (e.g., NACE TM0284) is conducted on specimens or samples extracted from finished products (e.g., components, equipment) for wet sour environment like line pipes, plates, coils, flanges, vessels, and fittings that are used for extraction, treatment, transportation or storage of crude containing water and $H_2S$. Such finished products may be made from HIC resistant material (e.g., hot rolled coil or plate of steel alloy composition having a specific Heat number) that has already been tested for HIC compliance and has been qualified as HIC resistant prior to applying any stress (e.g., cold forming) to the steel alloy. However, Inventors of the present disclosure conducted numerous experiments to determine that even if the source HIC resistant material has been tested and qualified as being resistant to HIC for sour service, once the source material is cold worked on (e.g., fabrication, casting, pressing, and the like) by applying stress to convert the material from a plate or coil of metal into a finished component (e.g., line pipe, flange, fitting, or any other equipment manufactured or fabricated from the Heat number of the HIC resistant source material), the resulting finished product may lose its resistance to HIC (and specifically, SOHIC), and therefore, become unfit for sour service use.

For example, a HIC resistant material candidate with a specific chemical element composition (e.g., hot rolled coil or plate with a given Heat number) may be manufactured at a steel mill, and a sample (e.g., HIC sample, HIC specimen, HIC coupon, non-stressed sample, non-curved sample) may be extracted from the HIC resistant material candidate and subjected to standardized HIC testing (e.g., NACE TM0284 test). The HIC sample at the steel mill may pass the HIC test based on measured values for predetermined HIC resistance criteria being not greater than corresponding predetermined maximum threshold values (e.g., CLR≤15%, CTR≤5%, and CSR≤2%) thereby qualifying the HIC resistant material candidate as being adequately resistant to HIC, and therefore, fit for manufacturing equipment to be used in sour service. Subsequently, the qualified HIC resistant material may be shipped from the steel mill to a pipe mill or otherwise be used for manufacturing (e.g., casting, cold forming, fabricating) the sour service equipment (e.g., line pipe, flanges, fittings and the like). After manufacturing the equipment at the pipe mill from the received qualified HIC resistant material, a sample (e.g., stressed sample, bent sample, curved sample, SOHIC sample, SOHIC specimen, SOHIC coupon) may be extracted from the manufactured equipment (e.g., from a base metal of a welded pipe) and subjected to the standardized HIC testing. This curved SOHIC sample extracted from the manufactured equipment may fail the HIC (SOHIC) test (e.g., CLR>15%, CTR>5%, and/or CSR>2%) despite the component being manufactured from qualified HIC resistant material that previously passed the HIC test.

If HIC (SOHIC) failure is detected at this late stage (e.g., after component manufacture at the pipe mill), the newly manufactured and tested components (e.g., pipes, plates, coils, flanges, vessels, fittings, and the like) will be rejected for sour service use. This late stage rejection results in a negative cost impact due to the required retesting, scrapping, cutting and segregating of the failed manufactured equipment. In addition, the late stage rejection will cause project schedule delay due to slow release of tested equipment and the long lead-time required to procure plates/coils to manufacture new equipment.

In order to overcome the above problems, the present disclosure proposes a method and system for performing a guided bend process on the qualified HIC resistant material (e.g., hot rolled or raw plate or coil material at the steel mill having a specific Heat number) to simulate the cold forming and resultant stress that will be applied to the material subsequently during component (e.g., pipe) manufacture at a pipe mill. That is, unlike conventional techniques that test for (SOHIC) HIC failure after component manufacture, techniques disclosed herein look to simulate the stress applied during equipment (e.g., pipe) forming through a guided bending process on the qualified HIC resistant material (e.g., plate/coil strip) at the steel mill to ensure that the effect of cold forming on the qualified HIC resistant material is taken into consideration prior to shipping the material to the pipe mill or prior to using the material for sour service equipment manufacture.

The guided bend process may be applied by supporting a middle portion in a width direction of a plate piece (e.g., plate specimen) of the qualified HIC resistant material on a female die and applying force with a male die through the plate piece into the female die to develop a predetermined U-shaped bent portion in the qualified HIC resistant material plate piece. Dimensions of the male and female dies, and the resulting U-shaped bent portion are predetermined to simulate the subsequent cold forming that will be applied during manufacture of equipment or components from the qualified HIC resistant material. Cold formation induced by the guided bend process will result in imparting microscopic stresses to the qualified HIC resistant material, leading to potential HIC damage if the material is not properly manufactured to resist this type of environmental cracking. Then, a bent sample (e.g., 20 mm wide by 100 mm long coupon; SOHIC sample, SOHIC specimen, SOHIC coupon, stressed sample, curved sample, and the like) may be extracted from a U-shaped bent portion of the qualified HIC resistant material plate piece, and after performing HIC testing per NACE TM0284 on the extracted SOHIC sample, the SOHIC sample may be examined by metallographic sectioning to calculate a value for at least one predetermined resistance criteria (e.g., CLR, CTR, and/or CSR) for each metallographic section, and determine whether the calculated value for the predetermined resistance criteria is within a corresponding acceptable predetermined maximum threshold value (e.g., CLR≤15%, CTR≤5%, and/or CSR≤2%). In case of HIC failure (e.g., SOHIC failure) being detected in the curved sample, the qualified HIC resistant material (e.g., Heat number corresponding to the qualified HIC resistant material) will be rejected prior to sending or otherwise using the qualified HIC resistant material for equipment manufacture, thereby avoiding the negative impacts of shipping or otherwise using the material to manufacture equipment that will ultimately be deemed unfit for its intended use, or waiting for the test to be conducted after the equipment manufacturing process.

ANSI/NACE TM0284-2016, Evaluation of Pipeline and Pressure Vessel Steels for Resistance to Hydrogen-Induced Cracking (HIC): HIC is a stepwise cracking that occurs in carbon steel in an H$_2$S-containing water environment due to absorption of atomic hydrogen. The extension of this type of cracking parallel to the rolling direction of steel coil or plate forms stepwise cracking. HIC propagates through a trap site in the material such as inclusion/matrix interfaces and does not require any external stress. A measure of successful HIC resistance of equipment or components used in sour service applications (e.g., pipelines, plates, coils, flanges, vessels, and fittings that are used for extraction, treatment, transportation and storage) is usually assessed through standardized corrosion tests such as NACE TM0284 on plate samples which evaluate the steel's susceptibility to HIC in reproducible service conditions. Details of test sample preparation, test solution and testing as per the NACE TM0284 standard are described below.

FIG. 1 shows schematic diagram 100 illustrating the orientation and faces to be examined of sample 120 undergoing HIC testing, in accordance with one or more embodiments. As shown in FIG. 1, a full thickness (≤30 mm) sample (e.g., HIC sample, HIC coupon, HIC specimen, non-stressed sample, non-bent sample) 120 of 100±1 mm long and 20±1 mm wide with longitudinal axis aligned with a principal rolling direction 110 of material 105 (e.g., hot rolled coil, plate, or strip of HIC resistant material candidate having a specific Heat number being tested for HIC resistance) is cut (e.g., extracted, obtained) from the source material 105. For plates 105 thicker than 30 mm, overlapping samples are taken till the whole thickness is covered in order to ensure central region of the plate is represented.

The HIC test is conducted based on predefined solutions, pH level, and H$_2$S concentration specified in NACE TM0284 (e.g., test conditions). NACE TM0284 describes two test solutions, Solution A and Solution B. In NACE TM0284 HIC testing, test specimens are usually exposed to a sour solution containing H$_2$S at a pressure of 1 bar for 96 hours. H$_2$S purity of 99.5% is used in testing. In NACE TM0284 Solution A, sodium chloride (NaCl) and acetic acid (CH$_3$COOH) are dissolved in distilled or deionized water saturated with H$_2$S gas at ambient temperature and pressure. In NACE TM0284 solution B, synthetic seawater solution is saturated with H$_2$S at ambient temperature and pressure. The reagents for Test Solution A are nitrogen gas for purging, H$_2$S gas, NaCl, CH$_3$COOH, and distilled or deionized water. The reagents for Test Solution B are nitrogen gas for purging, H$_2$S gas, and synthetic seawater. In case of HIC testing under NACE TM0284 Solution A, the pH at the start of the test shall be measured immediately after H$_2$S saturation and shall be within the range of 2.7 to 3.3. In case of HIC testing under NACE TM0284 Solution B, the pH shall be measured immediately after H$_2$S saturation and shall be within the range of 4.8 to 5.4. At the end of the HIC test, the pH for Solution A shall not exceed 4.0 for the test to be valid, and the pH shall be within the range of 4.8 to 5.4 for the test to be valid. The temperature of the test solution (A or B) during contact with the sample (e.g., HIC sample 120) shall be 25±3° C. (77±5° F.). Each sample shall be 100±1 mm (4.00±0.04 in) long by 20±1 mm (0.80±0.04 in) wide. Above specifications for NACE TM0284 are generally referred to here as "test conditions."

In case of HIC testing under NACE TM0284 Solution A, sample 120 for HIC testing is immersed in a sealed vessel containing 5% NaCl and 0.5% acetic acid in distilled water and purged with H$_2$S gas resulting in a pH of 3. After 96 hrs of exposure to the corrosive test solution termed Solution A, sample 120 is subject to metallographic sectioning along the dashed-lines at 115A, 115B, and 115C for analysis as shown in FIGS. 1 and 2.

FIG. 1 shows the manner in which the sample pieces 125A, 125B, 125C, and 125D (e.g., HIC sample pieces) are sectioned for metallographic evaluation for any cracks generated. Reference numerals 115A, 115B and 115C indicate the faces of sample pieces 125A, 125B, 125C, and 125D to be examined/tested for cracks. Solution A offers the most severe corrosive atmosphere and the test itself is very rigorous in evaluating HIC resistance. A measure of successful HIC resistance is interpreted based on acceptable maximum threshold values (e.g., percentage values) for predetermined HIC resistance criteria (e.g., CLR, CSR, and CTR) using crack dimensions as indicated in FIG. 2.

Figure 2:
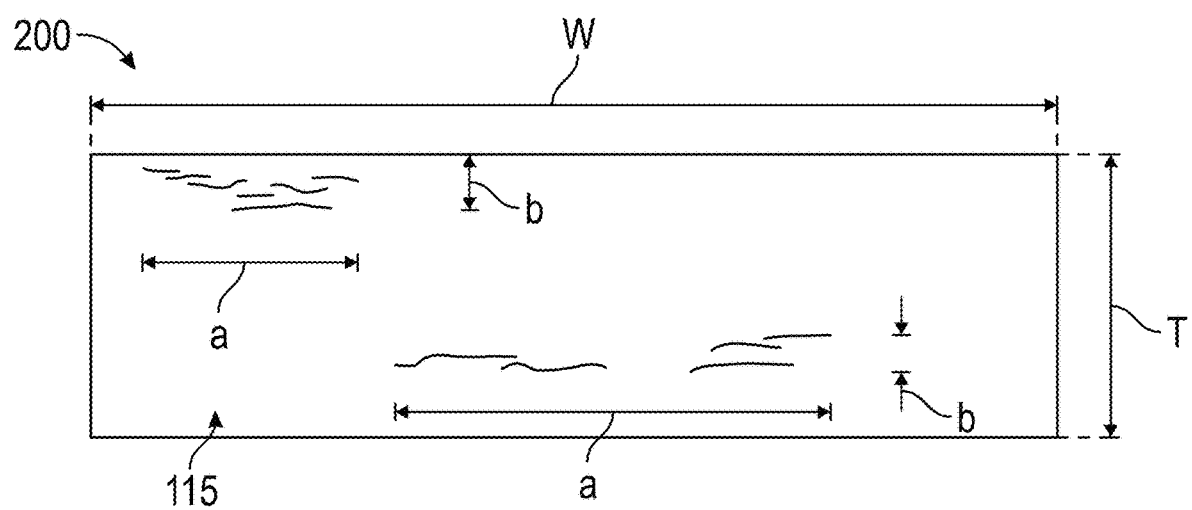
FIG. 2 depicts the face of each piece to be analyzed and describes the variables used to calculate Crack Length Ratio (CLR), Crack Sensitivity Ratio (CSR) and Crack Thickness Ratio (CTR) in standardized HIC testing, in accordance with one or more embodiments.

FIG. 2 depicts cross-sectional view 200 of face 115 (e.g., face at 115A, 115B, or 115C in FIG. 1) of a piece (e.g., one of sample pieces 125A, 125B, 125C, and 125D in FIG. 1) to be analyzed to calculate CLR, CSR and CTR percentage values. Equations used to calculate CLR, CSR and CTR are as follows.

$$CSR = \frac{\sum (a \times b)}{(W \times T)} \times 100\%$$

$$CLR = \frac{\sum a}{W} \times 100\%$$

$$CTR = \frac{\sum b}{T} \times 100\%$$

As shown in FIG. 2, the face (e.g., face at 115A, 115B, or 115C in FIG. 1) of the piece (e.g., 125A, 125B, 125C, or 125D in FIG. 1) to be analyzed has a width W and a thickness T. The CLR is defined as the sum of the width dimensions of all cracked sections "a" (i.e., Σa) divided by the face width W and multiplied by 100 to result in a percentage. The CSR is sum of the width dimensions of each cracked section "a" times the thickness of that section "b" for all cracked sections (i.e., Σ(a×b)), which sum is then divided by the product of the face width W and the face thickness T (i.e., W×T) and again multiplied by 100 to result in a percentage. Finally, the CTR is defined as the sum of the thickness dimensions of all cracked sections "b" (i.e., a) divided by the face thickness T and multiplied by 100 to result in a percentage.

Thus, after completion of HIC testing as per NACE TM0284, the CLR, CTR, and CSR are calculated for one or more metallographic section of the sample (e.g., HIC sample of HIC resistant material candidate undergoing testing for HIC resistance prior to cold forming or any applied or residual stress to the material candidate) to determine whether the calculated percentage values (or averaged values) meet predetermined thresholds. American Petroleum Institute (API) and International standards stipulate CLR, CTR and CSR values of ≤15%, ≤5% and ≤2%, respectively for HIC resistant linepipe grades (e.g., predetermined maximum threshold values for the respective predetermined HIC resistance criteria subsequent to the HIC testing for HIC sample of HIC resistant material candidate). Final CLR, CTR, and CSR percentage values for sample 120 may be calculated based on respective CLR, CTR, and CSR values for one or more of the faces (e.g., 115A, 115B, and 115C in FIG. 1) of one or more of the pieces (e.g., 125A, 125B, 125C, and 125D in FIG. 1) of sample 120.

As mentioned previously, the HIC test as per NACE TM0284 is used to qualify the HIC resistant material candidate (e.g., hot rolled coil or plate of carbon steel that has a specific Heat number and that has not been subject to any cold forming or applied/residual stress) to be used in wet sour applications containing $H_2S$ where HIC resistance is required. Once one or more HIC samples extracted from the Heat number of the HIC resistant material candidate have been determined to have passed the standardized HIC test (e.g., calculated CLR, CTR and CSR values of ≤15%, ≤5% and ≤2%, respectively), the source of the HIC samples (e.g., the specific Heat number) is determined to be qualified as a valid source of material for manufacturing equipment or components that are to be used in sour service.

For example, after manufacture of the specific Heat number of the hot rolled steel alloy coil or plate strip of the HIC resistant material candidate, a HIC sample (e.g., 120 in FIG. 1) may be extracted from the Heat number without subjecting the Heat number to any cold forming or applied or residual stress or any treatment, and the extracted HIC sample may be subject to the standardized HIC test as per the NACE TM0284 standard for determining resistance of the Heat number to HIC damage. After completion of the HIC testing for the HIC sample, the sample may be subject to metallographic evaluation as shown in FIGS. 1 and 2 to determine whether calculated respective ratio values of predetermined HIC resistance criteria (e.g., CLR, CTR, and/or CSR) are less than corresponding predetermined maximum threshold values. In response to determining that the calculated respective ratio values of the predetermined HIC resistance criteria for the HIC sample are less than the corresponding predetermined maximum threshold values (e.g., calculated CLR, CTR and CSR values of ≤15%, ≤5% and ≤2%, respectively), the Heat number from which the HIC sample was extracted is qualified as a valid source of material for manufacturing equipment (e.g., line pipes, plates, coils, flanges, vessels, and fittings) to be used in sour service. In particular, the specific Heat number of the qualified HIC resistant material manufactured at a steel mill may be considered qualified and "ready" for shipment to a subsequent site (e.g., a pipe mill) where the Heat number will be used for manufacturing (e.g., fabricating, cold working, cold forming, casting, pressing) equipment or components (e.g., line pipes, plates, coils, flanges, vessels, and fittings) for sour service use.

Subsequently, components or equipment may be manufactured from the qualified Heat number of the HIC resistant material. After manufacture of the equipment (e.g., line pipe), conventionally, HIC compliance is tested again by sectioning samples from a weld area and/or from a base metal of the manufactured equipment (e.g., at 90° and 180° from the weld area), and subjecting the samples to the standardized HIC testing for determining HIC resistance of the manufactured equipment that has undergone cold forming and/or applied or residual stress during the manufacturing process. The HIC test may be conducted as per the NACE TM0284 standard, where the sectioned sample (e.g., SOHIC sample, curved sample) is exposed to a wet sour $H_2S$ at a pressure value of 1 bar for a duration of 96 hours. After completion of the HIC (SOHIC) test, the sample will be investigated by metallographic sectioning for crack susceptibility as per the NACE TM0284 standard, and CLR, CTR and CSR will be calculated for each metallographic section.

When conducting the above conventional HIC (SOHIC) testing on line pipes (e.g., welded pipe) manufactured from qualified HIC resistant materials, international codes such as API 5 L require that samples be taken from the base metal of the manufactured pipe and may be extracted from the weld area, and at 90° and 180° from the weld area of the pipe for HIC testing (and specifically, SOHIC testing). Inventors of the present disclosure conducted numerous experiments and determined that samples extracted from the base metal of the manufactured line pipe that predominantly experience HIC failure (and more specifically, SOHIC failure) as evidenced by measured values exceeding respective predetermined maximum threshold values for predetermined resistance criteria (e.g., CLR, CTR, CSR) stipulated by industry standards, are generally at 180° from the weld. Inventors of the present disclosure further determined that samples extracted 180° from the weld from the manufactured line pipe correspond to a region that is at a middle in a width direction of the qualified HIC resistant material from which the line pipe was manufactured (e.g., middle of the hot rolled plate or coil of the qualified HIC resistant material). Therefore, Inventors of the present disclosure determined that the region at the middle of the qualified HIC resistant material (e.g., middle of the plate or coil) in the width direction is considered to be a high stress area that is most susceptible to SOHIC failure after being subjected to cold forming.

Inventors of the present disclosure further conducted numerous experiments to determine that the high stress area (corresponding to 180° from the weld in the finished pipe product) in the middle of the HIC resistant material (e.g., middle of the plate or coil) in the width direction, when tested prior to the cold forming (e.g., prior to the stress applied during pipe forming) did not show any indications of HIC failure, due to absence of the microscopic residual stresses and resulting micro-fissures imparted during cold forming. For example, the Inventors determined that CLR, CTR, and CSR values for a sample (e.g., HIC sample, HIC coupon, HIC specimen, non-stressed sample, and the like) that is extracted directly from the coil/plate of the qualified HIC resistant material at the steel mill prior to shipment of the material to the pipe mill for fabrication and that is extracted from a location corresponding to 180° from the weld of the subsequently manufactured line pipe (e.g., the high stress area), were 0% or within the respective predetermined maximum threshold values. However, when the same standardized HIC testing was performed after subjecting the qualified HIC resistant material to pipe forming at the pipe mill, and a sample (e.g., SOHIC sample, SOHIC coupon, SOHIC specimen, stressed or bent sample, and the like) extracted from the base metal of the manufactured pipe at 180° from the weld, the HIC (SOHIC) failure for the predetermined resistance criteria was detected (e.g., CLR>15%, CTR>5%, and/or CSR>2%).

Such late stage failure detection leads to wastage in the form of manufactured equipment that is not fit for its intended use, time and effort required for procuring new HIC resistant material, retesting, scrapping, recycling manufactured equipment that failed the SOHIC test, manufacturing new sour service equipment from the new HIC resistant material, and the like. In order to overcome the above problems, the present disclosure proposes a new method and system for performing a guided bend process on the qualified HIC resistant material prior to equipment manufacture to simulate the cold forming that will be applied during the subsequent equipment manufacture. HIC testing performed after the guided bend process thus takes into account the effect of cold forming that will be applied to the material during component manufacture, thereby determining at an earlier stage, whether sour service components manufactured from the qualified HIC resistant material will be adequately resistant to SOHIC. Details of the guided bend process and subsequent SOHIC testing performed on the bent sample (e.g., SOHIC sample, stressed sample, curved sample) are provided below in detail in connection with FIGS. 3-6.

Figure 3:
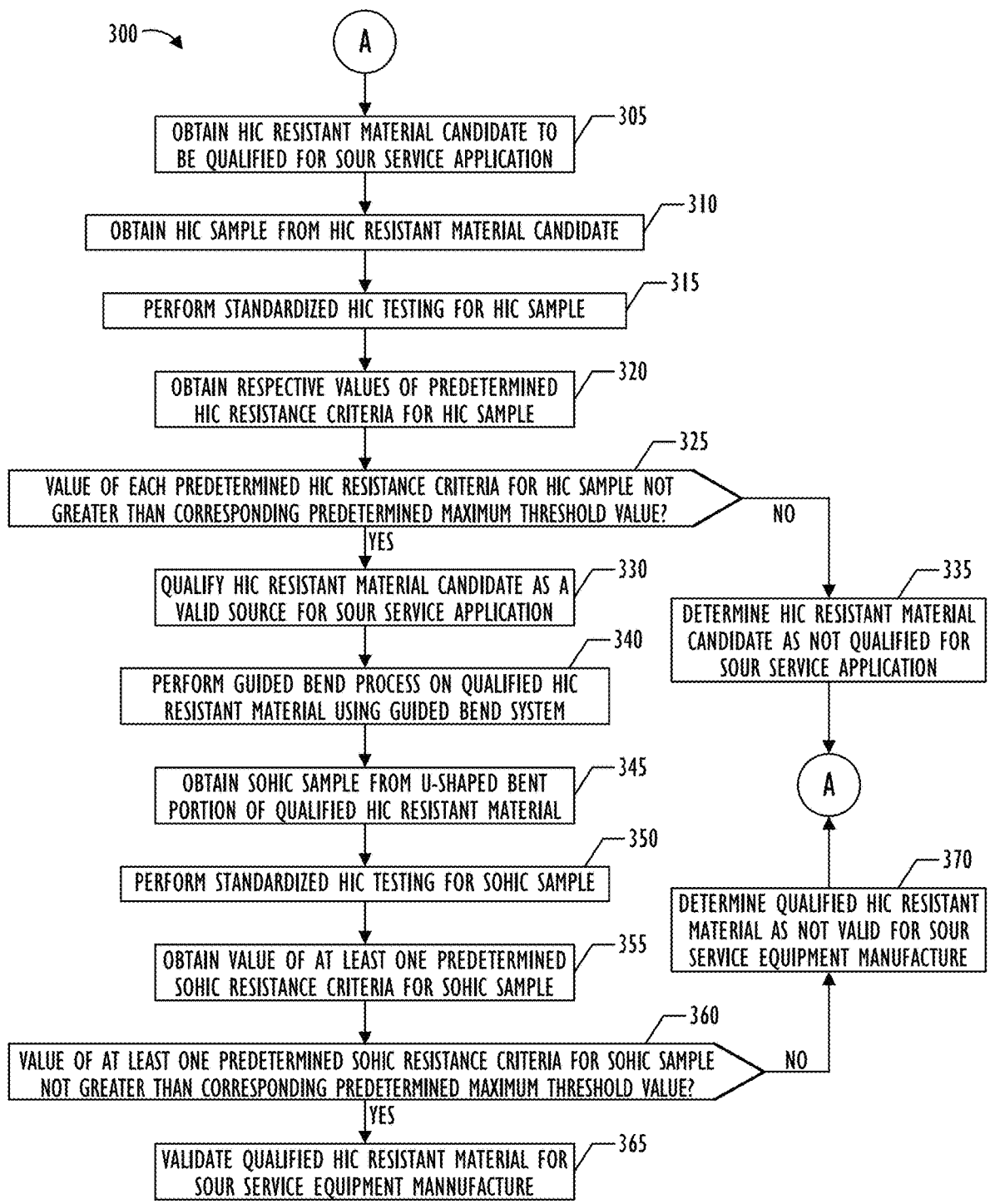
FIG. 3 is a flow chart that illustrates a method for performing standardized HIC testing for validating a HIC resistant material candidate for use in sour service applications, and further performing standardized HIC testing on the qualified HIC resistant material subjected to cold forming, in accordance with one or more embodiments.

FIG. 3 is a flow chart that illustrates method 300 for performing standardized HIC testing for validating a HIC resistant material candidate for use in sour service applications, and further performing standardized HIC testing on the qualified HIC resistant material after subjecting the material to cold forming to simulate the stress applied to the material during subsequent component (e.g., pipe) manufacture, in accordance with one or more embodiments. Method 300 begins at block 305 where a HIC resistant material candidate, that is undergoing standardized testing (e.g., NACE TM0284) for being qualified as adequately HIC resistant to be suitable for use in sour service applications, is obtained (e.g., selected, developed, manufactured, and the like). At block 305, the HIC resistant material candidate may be a manufactured hot rolled coil or plate strip material having a specific Heat number and a specific alloy composition. For example, the HIC resistant material candidate may be manufactured so that it is suitable for sour service use. The HIC resistant material candidate obtained at block 305 is in a "raw" form that has not been subjected to any cold forming or treatment. Therefore, no microscopic applied or residual stresses or resulting micro-fissures resulting from cold forming have been imparted to the HIC resistant material obtained at block 305.

Method 300 proceeds to block 310 where at least one HIC sample (e.g., non-stressed sample, non-curved sample) is obtained (e.g., extracted, cut, and the like) from the HIC resistant material candidate obtained at block 305. The HIC sample at block 310 may be extracted from the HIC resistant material candidate in a manner shown in FIG. 1. For example, the HIC sample at block 310 may be a full thickness (≤30 mm) sample of 100±1 mm long and 20±1 mm wide that is cut from the Heat number of the HIC resistant material candidate obtained at block 305 such that the longitudinal axis of the test sample is aligned with the principal rolling direction of the HIC resistant material candidate (FIG. 1).

At block 315, the at least one HIC sample obtained at block 310 is subjected to standardized HIC testing under the predetermined standardized conditions (e.g., test conditions dictated by NACE TM0284). For example, at block 315, HIC testing is performed as per Solution A of the NACE TM0284 standard, with a sodium chloride and acetic acid solution. In this case, at block 315, the HIC sample is immersed in a sealed vessel containing 5% NaCl and 0.5% acetic acid in distilled water and purged with $H_2S$ gas resulting in a pH of 3. After 96 hrs of exposure to the corrosive test solution termed Solution A, the HIC sample is subject to metallographic sectioning (e.g., each HIC sample may be metallographically sectioned for testing as shown in connection with FIGS. 1 and 2) for evaluation and analysis.

At block 320, respective values (e.g., percentage values, ratio values) of each predetermined HIC resistance criteria for the HIC sample are obtained (e.g., calculated, determined) based on the HIC testing performed on the HIC sample at block 315. The value for each of the predetermined HIC resistance criteria for the HIC sample may be calculated or obtained in a manner similar to the method of obtaining CLR, CTR, and CSR percentage values for sample 120 as shown in FIGS. 1 and 2. That is, for the HIC sample subject to HIC testing at block 315, metallographic evaluation may be performed for a plurality of pieces of the HIC sample (e.g., sample pieces 125A, 125B, 125C, and 125D of FIG. 1) after the HIC test for any cracks generated. That is, sectioned faces (e.g., faces at 115A, 115B and 115C in FIG. 1) of the HIC sample may be examined and tested for cracks. For example, at block 320, CLR, CTR, and CSR values for the HIC sample may be calculated as the respective values for the predetermined HIC resistance criteria. In some embodiments, each of CLR, CTR, and CSR values may be calculated by respectively averaging the CLR, CTR, and CSR values calculated for one or more of the faces (e.g., 115A, 115B, and 115C in FIG. 1) of one or more of the pieces (e.g., 125A, 125B, 125C, and 125D in FIG. 1) of HIC sample subject to the HIC testing at block 315.

Method 300 then proceeds to block 325 where it is determined whether the calculated values of the predetermined HIC resistance criteria for the HIC sample are not greater than corresponding predetermined maximum threshold values (e.g., percentage values). The maximum threshold values for the predetermined HIC resistance criteria (e.g., CSR, CTR, and/or CLR) are predetermined based on the level of HIC resistance required of the HIC resistant material candidate being tested, and may be preset by a user. For example, the maximum threshold values for CLR, CTR and CSR may be preset at 15%, 5% and 2%, respectively, based on API and International standards for HIC resistant line pipe grades. In this case, at block 325, it may be determined whether, for the HIC sample subjected to HIC testing at block 315, the average CSR≤2%, average CLR≤15%, and average CTR≤5%. As another example, the maximum threshold values for CLR, CTR and CSR may all be preset at 0%, to have the HIC resistant material candidate meet more stringent requirements for resistance to HIC. In this case, at block 325, it may be determined whether, for the HIC sample subjected to HIC testing at block 315, the average CSR, average CLR, and average CTR are all=0%.

If it is determined that the calculated values for the predetermined HIC resistance criteria for the HIC sample are not greater than corresponding predetermined maximum threshold values (YES at block 325), method 300 proceeds to block 330 where the corresponding manufactured HIC resistant material candidate (e.g., hot rolled coil or plate having a Heat number) obtained at block 305 is qualified as a valid source of material for use in sour service applications. That is, at block 330, it is determined that the HIC resistant material candidate obtained at block 305 meets the predetermined requirements for HIC resistance that are needed for using the material in sour service applications, and therefore, the HIC resistant material candidate obtained at block 305 (from which the HIC sample is extracted at block 310) is determined to be an acceptable source of HIC resistant material, and using the sourced material for manufacturing components that will be used in sour service environments. For example, for the HIC sample, when the average CSR≤2%, average CLR≤15%, and/or average CTR≤5%, the HIC resistant material candidate (e.g., a specific Heat number of a HIC resistant material candidate) is considered to be qualified for use in wet sour environments.

The source of the HIC resistant material candidate obtained at block 305 may be any suitable source. For example, the source may be any type of carbon steel material having a selected chemical element composition and made into coils or plates or strips, which need to be tested for HIC resistance adequacy to certify the material for use in wet sour environments. At block 330, since the candidate has passed the HIC test, this source of the HIC resistant material candidate obtained at block 305 is now considered to be qualified as a valid source for wet sour use. For example, if the source is a particular selected or manufactured Heat number of hot rolled coil or plate or strip, then the Heat number of the HIC resistant material candidate obtained at block 305 may be qualified as a valid source for use in sour service applications.

On the other hand, if it is determined that at least one of the calculated values for the predetermined HIC resistance criteria for the HIC sample is greater than a corresponding predetermined maximum threshold value (NO at block 325), method 300 proceeds to block 335 where the HIC resistant material candidate obtained at block 305 is determined to be not qualified for use in sour service applications. At block 325, HIC damage greater than the threshold amounts (as indicated by at least one of the calculated values for the predetermined HIC resistance criteria for the HIC sample being greater than a corresponding predetermined maximum threshold value) indicates that the HIC resistant material candidate from which the HIC sample was extracted is not fit for use in sour service applications that require high levels of HIC resistance.

Using such a low- or non-HIC resistant material candidate for manufacturing components like line pipes, plates, coils, flanges, vessels, and fittings for extraction, treatment, transportation and storage of crude containing water and $H_2S$ (e.g., wet sour service applications) would lead to cracking and breakage that would reduce the lifetime of the components, and cause leakage or catastrophic damage. By disqualifying such HIC resistant material candidate at block 335 (e.g., disqualifying the Heat number of the HIC resistant material candidate obtained at block 305, or other source identifier of the HIC resistant material candidate) use of such material for wet sour service applications is prevented. Once the HIC resistant material candidate obtained at block 305 is determined to be invalid for sour service use at block 335, method 300 returns to block 305 and the steps of method 300 are repeated to select a new HIC resistant material candidate, and perform the standardized HIC test for the new HIC resistant material candidate to determine its HIC resistance. For example, a new HIC resistant material candidate (e.g., having a new Heat number or a new source identifier) may be obtained, a new HIC sample from the new Heat number may be extracted, and the HIC test under NACE TM0284 standard, Solution A or B may be repeated for the new sample. By repeating steps 305-335 of method 300, HIC resistant material candidates that meet or exceed the desired level of HIC resistance during standardized HIC testing prior to cold forming can be identified and qualified to proceed to the next steps of method 300 for further testing for SOHIC.

As mentioned previously, the HIC resistant material candidate obtained at block 305 and qualified as being adequately HIC resistant at block 330 has not undergone any applied or residual stress or surface treatment prior to the standardized HIC test at block 315. To test the HIC resistant material qualified at block 330 for SOHIC resistance (e.g., resistance to HIC after the qualified HIC resistant material has been subject to stress by cold forming), at block 340, a guided bend process is performed. The guided bend process is performed at block 340 using guided bend system 400 of FIG. 4. Details of the guided bend process and system are discussed below in connection with FIGS. 4, 5A and 5B.

Figure 4:
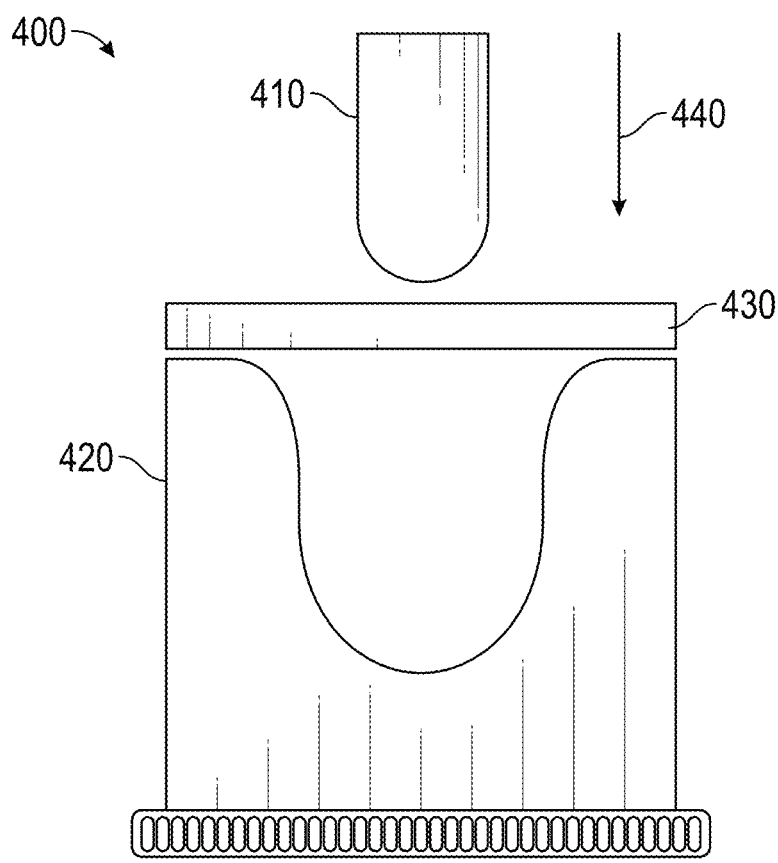
FIG. 4 is a schematic diagram of a system for performing a guided bend process on the qualified HIC resistant material to simulate the cold forming that will be applied to the qualified HIC resistant material during sour service equipment manufacture, in accordance with one or more embodiments.
Figure 5A:
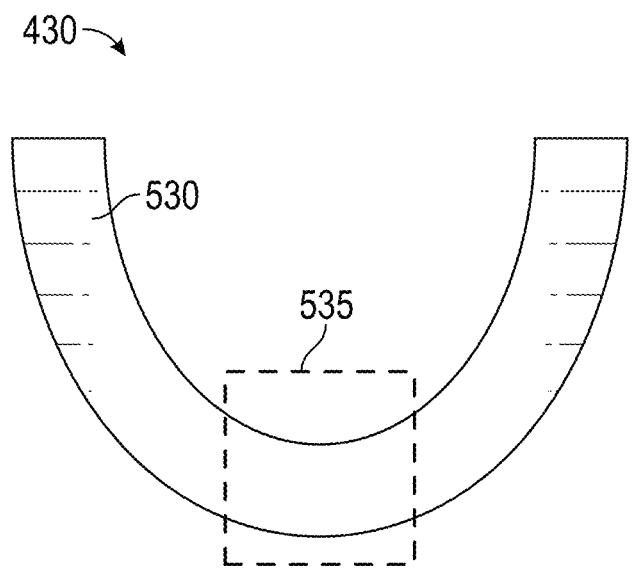
FIG. 5A is a schematic diagram illustrating a profile view of a U-shaped bent portion of the qualified HIC resistant material that has been subjected to the guided bend process by the guided bend system of FIG. 4, in accordance with one or more embodiments.
Figure 5B:
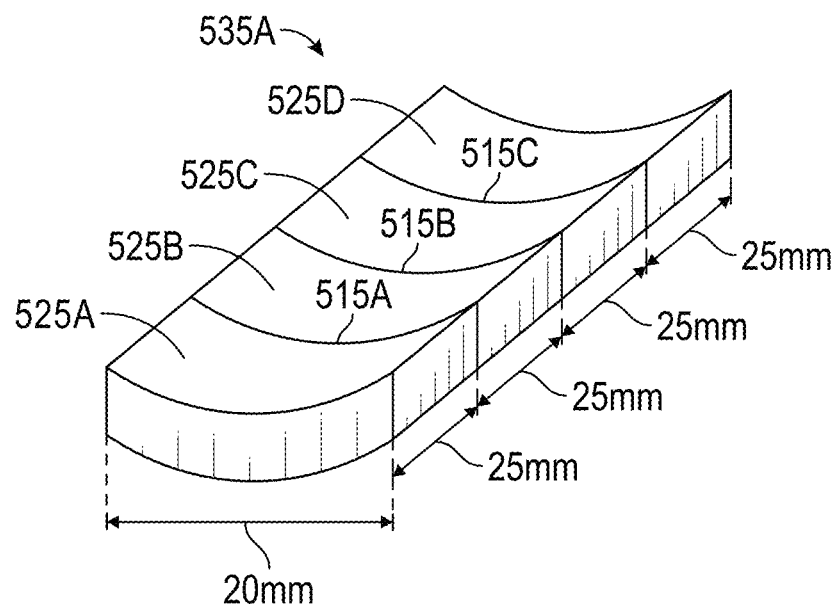
FIG. 5B is a schematic diagram illustrating a perspective view of a SOHIC sample extracted from the U-shaped bent portion of the qualified HIC resistant material of FIG. 5A, in accordance with one or more embodiments.

FIG. 4 is a schematic diagram of guided bend system 400 for performing a guided bend process on the qualified HIC resistant material (e.g., HIC resistant material qualified at block 330 of FIG. 3) to simulate the cold forming that will be applied to the qualified HIC resistant material subsequently during manufacture of sour service components or equipment (e.g., pipes, plates, coils, flanges, vessels, and fittings that are used for extraction, treatment, transportation or storage of crude containing water and $H_2S$), in accordance with one or more embodiments. FIG. 5A is a schematic diagram illustrating a profile view of U-shaped bent portion 530 of qualified HIC resistant material 430 of FIG. 4, in accordance with one or more embodiments. FIG. 5B is a schematic diagram illustrating a perspective view of SOHIC sample 535A extracted from region 535 of U-shaped bent portion 530 of FIG. 5A, in accordance with one or more embodiments.

As shown in FIG. 4, guided bend system 400 includes male die 410 and female die 420. Although not shown in FIG. 4, male die 410 is movably coupled to, and actuated by, an actuation system. The actuation system may be implemented using any suitable actuation mechanism (e.g., hydraulics, pneumatics, rack-and-pinion, electromechanical, and the like) to actuate male 410 with respect to the female die 420 with a predetermined pressing force in a direction indicated by arrow 440. In case HIC resistant material qualified at block 330 of FIG. 3 is a hot rolled coil or plate having a specific Heat number, qualified HIC resistant material 430, on which the guided bend process is performed by system 400, may be a plate piece (e.g., plate specimen) that is cut out from a middle portion of the qualified Heat number based on dimensions of the male and female dies 410 and 420 as shown in FIG. 4, so that a width of qualified HIC resistant material 430 matches a width of female die 420. The actuation system actuates one or both of the male and female dies 410 and 420 to sandwich qualified HIC resistant material 430 between male die 410 and female die 420 and impart a pressing/bending force to qualified HIC resistant material 430 in the direction indicated by arrow 440. Guided bend system 400 thus performs a U-shaped bending process to bend (and/or apply cold forming stress to) qualified HIC resistant material 430, and generate U-shaped bent portion 530 (FIG. 5A) in qualified HIC resistant material 430.

Characteristics and configuration (e.g., dimensions, shape, size, materials used, and the like of male and female dies 410 and 420; the amount of force applied by the actuation system to qualified HIC resistant material 430 during the guided bend process; position of qualified HIC resistant material 430 relative to male and female dies 410 and 420 during the guided bend process; the time duration during which the force is applied, and the like) of system 400, that produce resulting dimensions of U-shape bent portion 530 in qualified HIC resistant material 430, may be predetermined based on characteristics (e.g., size, dimensions, material thickness, high stress areas, and the like) of the sour service component that is to be manufactured from the Heat number of the qualified HIC resistant material 430. For example, if the Heat number of qualified HIC resistant material 430 is to be subsequently used to manufacture a line pipe having a particular pipe size or diameter, characteristics and configurations (e.g., die sizes, dimensions, force applied, time duration of force applied, positioning of material 430 relative to male and female dies 410 and 420) of system 400 may be preset such that U-shaped bent portion 530 produced in qualified HIC resistant material 430 will accurately simulate the cold forming ratio (or formability ratio) of the particular size or diameter of the line pipe that is to be subsequently manufactured from the Heat number.

Further, system 400 may be configured such that a peak bending force is applied to a predetermined middle portion (e.g., middle portion of hot rolled plate or coil or strip in a width direction that is perpendicular to the principal rolling direction of the qualified HIC resistant material) of qualified HIC resistant material 430 that corresponds to a predetermined high stress area. As explained previously, the predetermined middle portion of qualified HIC resistant material 430 has been identified to be a high stress area that has a higher likelihood of suffering from SOHIC damage subsequent to component manufacture. By subjecting the predetermined middle portion to the peak bending force by guide bend system 400, the applied or residual stress that will be suffered in the high stress area during subsequent component manufacture (e.g., pipe manufacture at a pipe mill) can be accurately replicated in the SOHIC sample and tested for SOHIC failure.

Thus, as shown in FIGS. 4 and 5A, guided bend system 400 positions qualified HIC resistant material 430 such that a middle portion of HIC resistant material 430 in a width direction thereof (left-right direction of HIC resistant material 430 as shown in FIG. 4) is subject to the peak bending force or stress when male die 410 presses down on HIC resistant material 430 into female die 420 in the direction shown by arrow 440, to form U-shaped bent portion 530. The middle portion of HIC resistant material 430 (that first comes into contact with male die 410) corresponds to region 535 shown in FIG. 5A. Region 535 of U-shaped bent portion 530 thus accurately simulates the cold forming ratio (or formability ratio) of the wet sour component (e.g., line pipe) that is to be subsequently manufactured from the Heat number of HIC resistant material 430. For example, region 535 of U-shaped bent portion 530 accurately simulates stress of the high stress area that has been predetermined to be most susceptible to HIC failure (e.g., SOHIC failure) in a welded line pipe manufactured from the Heat number of HIC resistant material 430 and that is at 180° from the weld.

The U-shaped bending process of system 400 as shown in FIGS. 4 and 5A may be performed in accordance with ASTM E290 Standard Test Methods for Bend Testing of Material for Ductility. Any surface imperfections resulting from the guided bend process shall result in rejecting U-shaped bent portion 530 of qualified HIC resistant material 430, and repeating the guided bend process with a new plate piece from the Heat number of the qualified HIC resistant material qualified at block 330. Cold formation induced by the guided bend process will result in imparting microscopic stresses to the material (e.g., to region 535), leading to potential HIC damage if the Heat number of qualified HIC resistant material 430 is not properly manufactured to resist this type of environmental cracking.

Returning to FIG. 3, after performing the guided bend process on the HIC resistant material qualified at block 330 with the guided bend system at block 340, method proceeds to block 345 where at least one SOHIC sample (e.g., stressed sample, bent sample, curved sample, SOHIC coupon) is obtained (e.g., extracted, cut, and the like) from the U-shaped bent portion of the qualified HIC resistant material that has been subjected to the guided bend process. The SOHIC sample at block 345 may be extracted from the U-shaped bent portion in a manner as shown in FIGS. 5A-5B. For example, the SOHIC sample at block 345 may be a full thickness (≤30 mm) sample 535A of 100±1 mm long and 20±1 mm wide that is cut as per NACE TM0284 from region 535 of U-shaped bent portion 530 so that the high stress area (corresponding to region 535) of the base metal of the manufactured component that is predetermined to be the most susceptible to HIC failure (e.g., SOHIC failure) is extracted from qualified HIC resistant material 430 as the SOHIC sample 535A. Thus, at block 345, extracted SOHIC curved sample 535A simulates the stress of a high stress region where maximum cold work will be applied during component manufacturing. At block 545, the longitudinal axis of the extracted SOHIC sample may be aligned with the principal rolling direction of the qualified HIC resistant material.

FIGS. 5A-5B (and block 345 of method 300) illustrate an example where one SOHIC sample is extracted from region 535 of U-shaped bent portion 530 of qualified HIC resistant material 430. However, this may not necessarily be the case. In some embodiments, two or more SOHIC samples may be extracted from U-shaped bent portion 530 for subsequent standardized SOHIC testing. The two or more SOHIC samples may each be from the same region 535 of U-shaped bent portion 530 on one or more plate pieces of qualified HIC resistant material 430 such that each of the two or more SOHIC samples may be linearly disposed along a longitudinal direction or principal rolling direction of the hot rolled coil or plate and extracted from the predetermined middle portion in the width direction of the qualified material. Alternately, the two or more SOHIC samples may include samples that are from U-shaped bent portion 530 and that are disposed in parallel along the longitudinal direction or principal rolling direction of qualified HIC resistant material 430. That is, the two or more SOHIC samples may include a first SOHIC sample 535A that is from region 535 of U-shaped bent portion 530, and one or more additional SOHIC samples that are extracted from additional lateral regions that are laterally disposed with respect to region 535 (e.g., regions to the left and/or right of region 535 of U-shaped bent portion 530 in FIG. 5A).

Method then proceeds to block 350, where the at least one SOHIC sample (e.g., bent sample, curved sample, stressed sample) obtained at block 345 is subjected to standardized HIC (SOHIC) testing under the predetermined standardized conditions (e.g., test conditions dictated by NACE TM0284). For example, at block 350, HIC testing is performed as per Solution A of the NACE TM0284 standard, with a sodium chloride and acetic acid solution. In this case, at block 350, the SOHIC sample is immersed in a sealed vessel containing 5% NaCl and 0.5% acetic acid in distilled water and purged with $H_2S$ gas resulting in a pH of 3. After 96 hrs of exposure to the corrosive test solution termed Solution A, the SOHIC sample is subject to metallographic sectioning (e.g., each SOHIC sample may be metallographically sectioned for testing as shown in connection with FIG. 5B) for evaluation and analysis.

At block 355, a value (e.g., percentage value, ratio value) of at least one predetermined SOHIC resistance criteria for the SOHIC sample is obtained (e.g., calculated, determined)

based on the SOHIC testing performed on the SOHIC sample at block 350. The value for the at least one predetermined SOHIC resistance criteria for the SOHIC sample may be calculated or obtained in a manner similar to the method of obtaining CLR, CTR, and/or CSR percentage values for the sample 120 as shown in FIGS. 1 and 2, and further explained in connection with FIG. 5B below.

FIG. 5B shows a schematic diagram illustrating the orientation and faces to be examined of curved SOHIC sample 535A undergoing HIC (SOHIC) testing. As shown in FIGS. 5A-5B, a full thickness (≤30 mm) sample 535A of 100±1 mm long and 20±1 mm wide with longitudinal axis aligned with the principal rolling direction of qualified HIC resistant material 430 is cut (e.g., extracted, obtained) from region 535 of U-shaped bent portion 530 of HIC resistant material 430. FIG. 5B shows the manner in which the sample pieces 525A, 525B, 525C, and 525D (e.g., SOHIC sample pieces) are sectioned for metallographic evaluation for any cracks generated. Reference numerals 515A, 515B and 515C indicate the faces of the sample pieces 525A, 525B, 525C, and 525D to be examined/tested for cracks as per NACE TM0284.

For example, at block 355, at least one of CLR, CTR, and CSR values for the SOHIC sample may be calculated as the value for the at least one predetermined SOHIC resistance criteria for one or more metallographic sections as per the NACE TM0284 standard. In some embodiments, the at least one predetermined SOHIC resistance criteria may be the CLR, and in this case, the CLR value may be calculated by averaging CLR values calculated for one or more of the faces (e.g., 515A, 515B, and 515C in FIG. 1) of one or more of the pieces (e.g., 525A, 525B, 525C, and 525D in FIG. 5B) of SOHIC sample subject to the HIC testing at block 350. At block 355, the extracted SOHIC specimen may also be subject to ultrasonic testing to ensure that there are no pre-existing cracks, prior to obtaining the value for the at least one predetermined SOHIC resistance criteria for the bent or curved sample. The at least one predetermined SOHIC resistance criteria for the SOHIC sample at block 355 may be the same as or different from the predetermined HIC resistance criteria for the HIC sample at block 320.

Method 300 then proceeds to block 360 where it is determined whether the calculated value of the at least one predetermined SOHIC resistance criteria for the SOHIC sample (that has been subject to the guided bend process) is not greater than the corresponding at least one predetermined maximum threshold value (e.g., percentage value). The maximum threshold value for the at least one predetermined SOHIC resistance criteria (e.g., CSR, CTR, and/or CLR) is predetermined based on the level of SOHIC resistance required of the qualified HIC resistant material that was subject to cold forming by the guided bend process at block 340 and that was tested for SOHIC resistance at block 345. For example, the maximum threshold value for CLR may be preset at 15%, based on API and International standards for HIC resistant line pipe grades. In this case, at block 360, it may be determined whether, for the SOHIC sample subjected to HIC testing at block 345, average CLR≤15%. As another example, the maximum threshold value for CLR may all be preset at 0%, to have the qualified HIC resistant material meet more stringent requirements for resistance to SOHIC after subjecting the material to cold forming. In this case, at block 360, it may be determined whether, for the SOHIC sample subjected to cold forming by the guided bend process at block 340 and tested for SOHIC at block 345, average CLR=0%.

The predetermined maximum threshold value for the corresponding predetermined SOHIC resistance criteria for the SOHIC sample at block 360 may be the same as the predetermined maximum threshold value for the corresponding predetermined HIC resistance criteria for the HIC sample at block 325. Alternately, the predetermined maximum threshold value for the corresponding predetermined SOHIC resistance criteria for the SOHIC sample at block 360 may be different from the predetermined maximum threshold value for the corresponding predetermined HIC resistance criteria for the HIC sample at block 325. For example, the predetermined maximum threshold value for the predetermined SOHIC resistance criteria for the SOHIC sample at block 360 may be set by an end user or by a pipe mill that is to manufacture components from the qualified resistant material plate or roll for sour service use.

If it is determined that the calculated value for the at least one predetermined SOHIC resistance criteria for the SOHIC sample is not greater than a corresponding predetermined maximum threshold value (YES at block 360), method 300 proceeds to block 365 where the HIC resistant material candidate qualified as a valid source of material for use in sour service applications at block 330 is further qualified as a valid source of material that is resistant to SOHIC (e.g., resistant to HIC subsequent to cold forming) and that is fit for manufacturing components (e.g., pipes, plates, coils, flanges, vessels, fittings, and the like) that can be used in sour service without risk of failure or leakage. For example, at block 365, it may be determined that the Heat number of the qualified HIC resistant material (qualified at block 330) meets the predetermined requirements for SOHIC resistance that are needed for using the material to manufacture sour service compatible components, and therefore, the Heat number of the qualified resistant material (which is subject to the guided bend process at block 340 and from which the curved SOHIC sample 535A is extracted at block 345) is determined to be acceptable for shipping to a pipe mill where sour service components like line pipes will be manufactured from the Heat number. For example, for the SOHIC (e.g., bent or stressed) sample 535A, average CLR may be measured as less than the preset threshold of 15%, and therefore, the qualified HIC resistant material (e.g., a specific Heat number) may be considered to be adequately resistant to SOHIC damage, and therefore, fit for shipping to the pipe mill for component or equipment manufacture from the Heat number.

On the other hand, if it is determined that the calculated value for the at least one predetermined SOHIC resistance criteria for the SOHIC sample is greater than the corresponding predetermined maximum threshold value (No at block 360), method 300 proceeds to block 370 where the qualified HIC resistant material qualified for HIC resistance prior to cold forming is deemed disqualified or unfit as a valid source of material that is resistant to SOHIC, after cold forming is applied to the qualified HIC resistant material. That is, at block 370, the Heat number of the qualified HIC resistant material qualified at block 330 prior to cold forming is deemed unfit for manufacturing components (e.g., pipes, plates, coils, flanges, vessels, fittings, and the like) that can be used in sour service, because the qualified HIC resistant material has failed the HIC (SOHIC) test after cold forming was applied to the material. At block 360, SOHIC damage greater than the threshold amount (as indicated by the calculated value for the predetermined SOHIC resistance criteria for the SOHIC sample being greater than the corresponding predetermined maximum threshold value; e.g., CSR>2%, CLR>15%, and/or CTR>5%) indicates that the qualified HIC resistant material, which was subjected to bending and from which the curved SOHIC was extracted, is not fit for use in sour service applications that require high levels of HIC (SOHIC) resistance even after the material is subject to applied or residual stress during cold forming work.

Using such a low- or non-SOHIC resistant material for manufacturing components like line pipes, plates, coils, flanges, vessels, and fittings for extraction, treatment, transportation and storage of crude containing water and $H_2S$ (e.g., wet sour service applications) would lead to cracking and breakage that would reduce the lifetime of the components, and cause leakage or catastrophic damage. By disqualifying such HIC resistant material (even though the material was found to be resistant to HIC prior to cold forming) block 370 (e.g., disqualifying the Heat number of the qualified HIC resistant material, or other source identifier of the qualified HIC resistant material) use of such material for component manufacture is prevented. Further, since the qualified HIC resistant material was subject to cold forming using the guided bend process by guided bend system 400 of FIG. 4, qualified HIC resistant material that fails the SOHIC test subsequent to cold forming can be detected prior to using the qualified HIC resistant material for component or equipment manufacture or prior to shipping the qualified HIC resistant material to the pipe mill for manufacture of the components (e.g., line pipes, plates, coils, flanges, vessels, and fittings), thereby increasing operational efficiencies, and preventing wasteful manufacture of wet sour equipment that will ultimately be rejected for SOHIC failure.

Once the qualified HIC resistant material is determined to be invalid or not qualified for sour service equipment manufacture or shipping to the pipe mill from the steel mill (block 370), method 300 returns back to block 305 and the steps of method 300 are repeated again for a new HIC resistant material candidate, to identify a new qualified HIC resistant material that will be resistant to HIC damage not only before it is subjected to stress by cold forming, but also after the cold forming by the guided bend process of FIG. 4. Further, since each qualified HIC resistant material (e.g., each new qualified Heat number of manufactured hot rolled coil or plate or strip of HIC resistant material that has been tested for HIC prior to applying stress to the material) is tested for SOHIC damage earlier in the process (e.g., before shipping the Heat number to the pipe mill for pipe manufacture, or before actual manufacture of sour service equipment from the qualified HIC resistant material), wastage of resources resulting from later stage rejection of the qualified HIC resistant material (e.g., after shipping to the pipe mill where the Heat number is used to manufacture components, after manufacture of the components from the qualified Heat number) is prevented, and operational efficiency is improved. Further, since the guided bend process according to the present disclosure applies the same cold forming ratio or formability ratio to a predetermined region (e.g., predetermined middle portion) of the qualified HIC resistant material (e.g., plate) as will be applied to the high stress region of the manufactured component (e.g., 180° from the weld area of the line pipe), resistance to SOHIC for the qualified HIC resistant material subsequent to cold forming can be accurately tested, without actually having to manufacture the components from the qualified Heat number.

Thus, by repeating steps 305-370 of method 300, qualified HIC resistant materials that are resistant to HIC even after cold forming (e.g., SOHIC resistant materials) can be identified more efficiently and with less costs. For example, the failed Heat number of qualified HIC resistant material will be rejected prior to sending the material to pipe manufacturing to avoid the negative impacts stated above of the conventional HIC testing methods that are implemented subsequent to component manufacture at the pipe mill. With the present method, the steel mill will be able to conduct failure analysis in case of SOHIC failure and evaluate the type, distribution, and amount of inclusions in the qualified HIC resistant material, thereby eliminating the time and cost that will be invested in shipping the material to the pipe mill and waiting for the test be conducted after the pipe manufacturing process. The material will be also investigated for centerline segregation. The accelerated test of the present disclosure will result in eliminating heavy cost and disruption to project schedule by preventing shipment of the raw material to pipe mill and waiting for the test be conducted after the pipe manufacturing process.

Experiment

Figure 6:
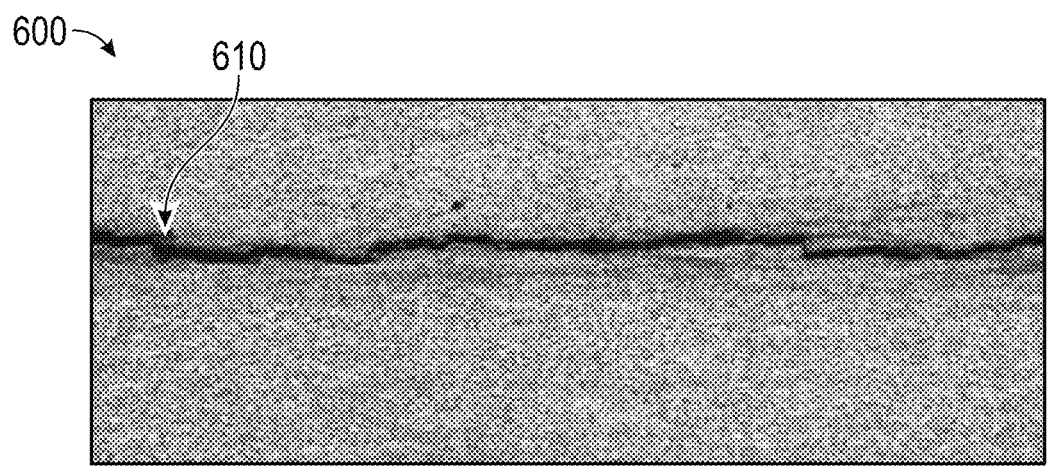
FIG. 6 is a photomicrograph showing microstructures indicating SOHIC failure of a sample subjected to conventional SOHIC testing, in accordance with one or more embodiments.

Inventors of the present disclosure have conducted experiments on manufactured components (e.g., ERW API 5 L X65 pipe) to identify the problem whereby even qualified HIC resistant material (that has been tested as being adequately HIC resistant prior to cold forming) may lose the resistance to HIC once the material has been subjected to cold forming work during component manufacture. Specifically, Inventors of the present disclosure conducted a HIC test (SOHIC test) on a curved specimen extracted from the middle of a API 5 L X65 pipe (e.g., manufactured component) made from HIC qualified carbon steel plate. The HIC test was conducted as per NACE TM0284, solution A. The HIC test results revealed average CLR of 17%. FIG. 6 is a photomicrograph 600 showing the microstructures 610 indicating SOHIC failure of the curved sample subsequent to SOHIC testing of the curved specimen extracted from the middle of the API 5 L X65 pipe made from the HIC qualified carbon steel plate. As shown in FIG. 6, band structure caused by segregation was observed along with the cracks. In case the predetermined acceptable threshold value for the average CLR is set at 15%, the measured value of average CLR of 17% is beyond the acceptance criteria for SOHIC qualification, thereby leading to rejection of the manufactured API 5 L X65 pipe and the HIC qualified carbon steel plate from which the pipe was manufactured.

The chemical analysis of the HIC qualified carbon steel plate revealed C: 0.047%, Si:0.19%, Mn:1.25%, P:0.0044%, S:0.0004%, Cu:0.24%, Ni:0.13%, Cr:0.22%, Mo:0.09%, Nb:0.044%, Ti:0.007%, Ca:0.0025%, B:0.0002%, and N:0.00385%. In the above example, the content of S was 4 ppm and the content of Ca 25 ppm. Inventors of the present disclosure conducted experiments and inclusion analysis to determine that Ca is the major element of the inclusions. Further, EDS analysis of the inclusions inside the cracks (610 in FIG. 6) revealed the presence of Si and Ca—Al oxide. Based on the Experiments, Inventors of the present disclosure determined that Ca content should be controlled to be at a lower level along with minimizing the sulfur content. The following Table provides examples of the qualified HIC resistant material that is resistant to HIC even after cold forming or pipe manufacture.

| Example # | Material Grade | Material type and Dimension | Chemical Composition % | | | | | | | | Chemical Composition % | | | | | HIC Test Results after Cold Forming | | | |
|---|---|---|---|---|---|---|---|---|---|---|---|---|---|---|---|---|---|---|---|
| | | | C | Si | Mn | S | N | Cu | Mo | Cr | V | Nb | Ti | B | Ca | Ca/S | CLR % | CTR % | CSR % Results |
| 1 | API 5L X60 Sour | Steel Plate Wall thickness: 12.7 mm Width: 2358 mm | 0.047 | 0.361 | 1.40 | 0.0004 | 0.0038 | 0.027 | 0.028 | 0.32 | 0.049 | 0.044 | 0.003 | 0.0003 | 0.001 | 2.5 | 0 | 0 | 0 PASSED |
| 2 | API 5L X60 Sour | LSAW Pipe Diameter: 508 mm Wall thickness: 19.05 mm | 0.04 | 0.30 | 1.36 | 0.0005 | 0.004 | 0.01 | 0.01 | 0.28 | 0.04 | 0.03 | 0.01 | 0.0004 | 0.001 | 2 | 0 | 0 | 0 PASSED |
| 3 | API 5L X60 Sour | LSAW Pipe Diameter: 762 mm Wall thickness: 9.53 mm | 0.04 | 0.29 | 1.3 | 0.001 | 0.0035 | 0.01 | 0.01 | 0.27 | 0.001 | 0.03 | 0.01 | 0.0003 | 0.003 | 3 | 0 | 0 | 0 PASSED |

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (e.g., meaning having the potential to), rather than the mandatory sense (e.g., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means ±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise.

Many other embodiments will be apparent to those of skill in the art upon reviewing the above description. The scope of the subject matter of the present disclosure therefore should be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method for performing a standardized hydrogen induced cracking (HIC) test on a HIC resistant material for sour service application, the method comprising:
    extracting a HIC sample from a HIC resistant material candidate;
    performing a standardized HIC test on the HIC sample;
    calculating respective values of a plurality of predetermined HIC resistance criteria for the HIC sample subsequent to the standardized HIC test on the HIC sample;
    determining whether the calculated respective values of the plurality of predetermined HIC resistance criteria for the HIC sample are not greater than corresponding predetermined maximum threshold values;
    qualifying the HIC resistant material candidate for a guided bend process in response to determining that the calculated respective values of the plurality of predetermined HIC resistance criteria for the HIC sample are not greater than the corresponding predetermined maximum threshold values;
    performing the guided bend process on the qualified HIC resistant material by supporting a plate specimen obtained from the qualified HIC resistant material on a guided bend system and applying force with male and female dies of the guided bend system to develop a predetermined U-shaped bent portion in the plate specimen;
    extracting a SOHIC sample from the U-shaped bent portion in the plate specimen;
    performing the standardized HIC test on the SOHIC sample;
    calculating a value of at least one predetermined SOHIC resistance criteria for the SOHIC sample subsequent to the standardized HIC test on the SOHIC sample;
    determining whether the calculated value of the at least one predetermined SOHIC resistance criteria for the SOHIC sample is not greater than a corresponding predetermined maximum threshold value; and
    validating the qualified HIC resistant material for manufacturing a sour service component in response to determining that the calculated value of the at least one predetermined SOHIC resistance criteria for the SOHIC sample is not greater than the corresponding predetermined maximum threshold value.

2. The method according to claim 1, wherein extracting the SOHIC sample from the U-shaped bent portion in the plate specimen comprises cutting a curved or bent sample having predefined dimensions as per a standardized NACE TM0284 corrosion test from a predetermined middle portion of the plate specimen on which the guided bend process has been performed.

3. The method according to claim 2, wherein a stress applied to the predetermined middle portion of the plate specimen to develop the predetermined U-shaped bent portion simulates a stress applied during a subsequent cold forming to a high stress region of the sour service component.

4. The method according to claim 3, wherein the manufactured sour service component is a line pipe having a given pipe diameter, wherein the guided bend process is performed on the plate specimen of the qualified HIC resistant material to develop the predetermined U-shaped bent portion whose dimensions simulate dimensions of the line pipe having the given pipe diameter, and wherein the high stress region of the line pipe is substantially at 180° from a weld area of the line pipe.

5. The method according to claim 1, wherein the standardized HIC test is a standardized NACE TM0284 corrosion test, and wherein the SOHIC sample is immersed in a corrosive test Solution A or a corrosive test Solution B, as defined by the NACE TM0284 corrosion test, during the test.

6. The method according to claim 5, wherein the HIC resistant material candidate is a hot rolled coil or plate of a carbon steel alloy composition that has a particular Heat number and that has not been subjected to cold forming prior to the guided bend process.

7. The method according to claim 1, wherein the SOHIC sample is a curved or bent sample that is extracted from the plate specimen of the qualified HIC resistant material such that a longitudinal direction of the SOHIC sample is aligned with a principal rolling direction of the qualified HIC resistant material.

8. The method according to claim 7, further comprising:
    metallographically sectioning the HIC sample into a plurality of pieces subsequent to the standardized HIC test on the HIC sample;
    analyzing one or more faces of one or more of the plurality of pieces of the HIC sample to calculate a Crack Length Ratio (CLR), a Crack Sensitivity Ratio (CSR), and a Crack Thickness Ratio (CTR), wherein the calculated CLR, CSR, and CTR are the respective values of the plurality of predetermined HIC resistance criteria for the HIC sample calculated subsequent to the standardized HIC test on the HIC sample;

metallographically sectioning the SOHIC sample into a plurality of pieces subsequent to the standardized HIC test on the SOHIC sample; and analyzing one or more faces of one or more of the plurality of pieces of the SOHIC sample to calculate a CLR, wherein the calculated CLR is the value of the at least one predetermined SOHIC resistance criteria for the SOHIC sample calculated subsequent to the standardized HIC test on the SOHIC sample.

9. The method according to claim 8, wherein the predetermined maximum threshold values for the CLR, CSR, and CTR for the HIC sample are preset at 15%, 2%, and 5%, respectively, and wherein the predetermined maximum threshold value for the CLR for the SOHIC sample is preset at 15%, wherein the HIC resistant material candidate is qualified for the guided bend process in response to determining that the calculated respective values of the CLR, CSR, and CTR for the HIC sample subsequent to the HIC test are not greater than 15%, 2%, and 5%, respectively, and wherein the qualified HIC resistant material is validated for manufacture of the sour service component in response to determining that the calculated value of the CLR for the SOHIC sample subsequent to the standardized HIC test thereon is not greater than 15%.

10. The method according to claim 1, wherein qualifying the HIC resistant material candidate for the guided bend process comprises qualifying a given Heat number corresponding to the HIC resistant material candidate for the guided bend process, and wherein validating the qualified HIC resistant material comprises validating the given Heat number for the manufacture of the sour service component.

11. The method according to claim 10, further comprising invalidating the given Heat number for manufacturing the sour service component in response to determining that the calculated value of the at least one predetermined SOHIC resistance criteria for the SOHIC sample is greater than the corresponding predetermined maximum threshold value.

12. The method according to claim 1, further comprising extracting a plurality of SOHIC samples from the qualified HIC resistant material on which the guided bend process has been performed, wherein the qualified HIC resistant material is validated for manufacturing the sour service component in response to determining that the calculated value of the at least one predetermined SOHIC resistance criteria for each of the plurality of SOHIC samples is not greater than the corresponding predetermined maximum threshold value.

13. A method for performing a guided bend process on a qualified HIC resistant material, the method comprising:

extracting a plate specimen from a qualified HIC resistant material having a Heat number;

supporting the plate specimen on a female die of a guided bend system and applying a force with a male die of the guided bend system to a predetermined middle portion of the plate specimen to develop a U-shaped bent portion in the plate specimen;

extracting a curved sample from the predetermined middle portion having the U-shaped bent portion, wherein the curved sample simulates a cold forming ratio of a line pipe having a particular pipe diameter that is to be subsequently manufactured from the qualified Heat number;

performing a standardized HIC test on the extracted curved sample;

calculating respective values of a plurality of predetermined SOHIC resistance criteria for the curved sample subsequent to the standardized HIC test on the curved sample;

determining whether the calculated respective values of the plurality of predetermined SOHIC resistance criteria for the curved sample are not greater than corresponding predetermined maximum threshold values; and validating the qualified Heat number for manufacturing the line pipe having the particular pipe diameter in response to determining that the calculated respective values not greater than the corresponding predetermined maximum threshold values.

14. The method according to claim 13, wherein a stress applied by the male die at the predetermined middle portion of the plate specimen during the guided bend process simulates a stress applied during a subsequent cold forming to a region of the line pipe that is substantially at 180° from a weld area of the line pipe.

15. The method according to claim 13, wherein the qualified HIC resistant material is predetermined to be resistant to HIC prior to cold forming based on standardized HIC testing on the HIC resistant material prior to the guided bend process.

16. The method according to claim 13, further comprising:

metallographically sectioning the curved sample into a plurality of pieces subsequent to the standardized HIC test on the curved sample; and analyzing one or more faces of one or more of the plurality of pieces of the curved sample to calculate a CLR, a CSR, and a CTR, wherein the calculated CLR, CSR, and CTR are the respective values of the plurality of predetermined SOHIC resistance criteria for the curved sample calculated subsequent to the standardized HIC test on the curved sample.

17. The method according to claim 16, wherein the predetermined maximum threshold values for the CLR, CSR, and CTR for the curved sample are preset at 15%, 2%, and 5%, respectively, wherein the qualified Heat number is validated for manufacturing the line pipe in response to determining that the calculated respective values of the CLR, CSR, and CTR for the curved sample are not greater than 15%, 2%, and 5%, respectively.

18. The method according to claim 16, wherein the predetermined maximum threshold values for the CLR, CSR, and CTR for the curved sample are each preset at 0%, wherein the qualified Heat number is validated for manufacturing the line pipe in response to determining that the calculated respective values of the CLR, CSR, and CTR for the curved sample are not greater than 0%.

19. A guided bend system for performing a guided bend process on a qualified HIC resistant material having a Heat number, the system comprising:

male and female dies having predetermined characteristics, wherein the predetermined characteristics of the male and female dies are preset based on characteristics of a line pipe having a given pipe diameter that is to be subsequently manufactured from the Heat number of the qualified HIC resistant material subjected to the guided bend process by the guided bend system, and wherein the female die is configured to support a plate specimen extracted from the qualified Heat number; and an actuation system that actuates the male die to apply a pressing force to a predetermined middle portion of the plate specimen supported on the female die to develop a U-shaped bent portion in the plate specimen;

wherein the guided bend system applies a stress at the predetermined middle portion of the plate specimen during the guided bend process to simulate a stress applied during a subsequent cold forming to a region of the line pipe that is substantially at 180° from a weld area of the line pipe.

20. A SOHIC sample for testing resistance to SOHIC, wherein:

the SOHIC sample is extracted as a curved sample from a predetermined middle portion of a plate specimen obtained from a Heat number of a qualified HIC resistant material, wherein the plate specimen has been subject to a guided bend process to develop a U-shaped bent portion at the predetermined middle portion of the plate specimen, and wherein the Heat number has been prequalified to be resistant to HIC based on a standardized NACE TM0284 corrosion test on a HIC sample extracted from the Heat number prior to the guided bend process, dimensions of the U-shaped bent portion simulate dimensions of a line pipe having a particular pipe diameter that is to be subsequently manufactured from the qualified Heat number, and a stress applied at the predetermined middle portion during the guided bend process simulates a stress applied during a subsequent cold forming to a region of the line pipe that is substantially at 180° from a weld area of the line pipe.

* * * * *